(12) United States Patent  (10) Patent No.: US 8,597,042 B2
King  (45) Date of Patent: Dec. 3, 2013

(54) CONNECTOR FOR IMPLANTABLE MEDICAL LEAD

(75) Inventor: Gary W. King, Fridley, MN (US)

(73) Assignee: Medtronic, Inc, Minneapolis, MN (US)

(*) Notice: Subject to any disclaimer, the term of this patent is extended or adjusted under 35 U.S.C. 154(b) by 28 days.

(21) Appl. No.: 13/262,998

(22) PCT Filed: Apr. 9, 2010

(86) PCT No.: PCT/US2010/030509
§ 371 (c)(1),
(2), (4) Date: Oct. 5, 2011

(87) PCT Pub. No.: WO2010/123701
PCT Pub. Date: Oct. 28, 2010

(65) Prior Publication Data
US 2012/0040548 A1  Feb. 16, 2012

Related U.S. Application Data

(60) Provisional application No. 61/171,129, filed on Apr. 21, 2009.

(51) Int. Cl.
*H01R 4/28* (2006.01)
(52) U.S. Cl.
USPC ............................. 439/341; 439/909
(58) Field of Classification Search
USPC .................................. 439/341, 909
See application file for complete search history.

(56) References Cited

U.S. PATENT DOCUMENTS

| 4,178,052 | A | * | 12/1979 | Ekbom et al. ............... 439/268 |
| 4,540,236 | A | * | 9/1985 | Peers-Trevarton ........... 439/159 |
| 4,614,395 | A | | 9/1986 | Peers-Trevarton |
| 4,637,672 | A | * | 1/1987 | Peterman et al. ............ 439/592 |
| 4,744,371 | A | | 5/1988 | Harris |
| 5,252,090 | A | | 10/1993 | Giurtino et al. |
| 5,257,622 | A | | 11/1993 | Hooper et al. |
| 5,275,620 | A | | 1/1994 | Darby et al. |
| 5,334,045 | A | * | 8/1994 | Cappa et al. ................ 439/506 |
| 5,439,391 | A | | 8/1995 | McEtchin et al. |
| 5,476,399 | A | * | 12/1995 | Porter ........................ 439/843 |
| 5,895,298 | A | * | 4/1999 | Faupel et al. ............... 439/729 |
| 6,716,070 | B2 | * | 4/2004 | Christensson ............... 439/859 |
| 7,777,140 | B2 | * | 8/2010 | Cappa et al. ............... 200/51.06 |
| 7,892,017 | B2 | * | 2/2011 | Meyer et al. ................ 439/435 |
| 2012/0040548 | A1 | * | 2/2012 | King ............................ 439/341 |

FOREIGN PATENT DOCUMENTS

WO  WO01/66184  9/2001

* cited by examiner

*Primary Examiner* — James Harvey
(74) *Attorney, Agent, or Firm* — Mueting Raasch & Gebhardt PA

(57) ABSTRACT

A connector (500) for operably coupling a medical lead to an implantable medical device includes first and second pivotably coupled elongate members (510, 520). Each of the first and second elongate members has (i) a proximal end portion (512, 522), and (ii) a distal end portion (514, 524) for engaging the lead. The lead has a proximal end portion having a shoulder. The first and second elongate members are pivotably coupled such that the distal end portions of the first and second elongate members are moveable to allow insertion of the lead proximally past the distal end portions of the elongate members and to allow the distal end portions to engage the lead distal the shoulder.

19 Claims, 9 Drawing Sheets

CONNECTOR FOR IMPLANTABLE MEDICAL LEAD

RELATED APPLICATIONS

This patent application is a 35 U.S.C. §371 national stage application based on PCT International Application No. PCT/US10/030509, filed Apr. 9, 2010, which claims priority to U.S. Patent Provisional Application Ser. No. 61/171,129, thed Apr. 21, 2009, the entire disclosure of each such related application being expressly incorporated herein by reference.

FIELD

This application relates to implantable medical devices; more particularly to devices that employ medical leads and connectors that electrically couple leads to the devices.

BACKGROUND

Implantable medical devices are used to treat a variety of diseases, and their use is increasing. Many implantable medical devices employ medical leads to deliver electrical therapy to a patient or to monitory patient parameters. The leads are connected to an active device, which is typically implanted in a subcutaneously in the patient, and extend from the implanted active device to a target location of the patient. Such devices generate or receive electrical signals that are transferred to or from a patient's tissue through electrodes disposed on a distal end portion of a lead. The proximal end portion of a lead typically contains a number of contact rings corresponding to the number of electrodes. Conductors run within and along the lead body and electrically couple the contact rings to the electrodes. The proximal end portion of the lead is inserted into a connector of the active medical device such that electrical contact is made between discrete contacts in the connector portion and the contact rings of the lead. The lead is then often secured to the connector portion of the signal generator via a set screw, which provides a compressive force on the lead, typically at one of the connector rings.

The set screw is typically tightened with a torque wrench to ensure proper tightening of the set screw. If the screw is tightened too loosely, the lead may come loose from the active device following implantation in the patient. If the screw is too forcefully tightened, damage to the lead may result. Accordingly, a good amount of time and care is taken to ensure proper tightening of the set screw.

Improved connectors for securing a lead relative to an implantable medical device would be desirable.

BRIEF SUMMARY

Among other things, screw-less connectors for securing a lead relative to an implantable medical device are described herein. Such connectors, in various embodiments, can be easier to implement than a set screw and torque wrench and may result in improved reliability.

In various embodiments, a connector includes first and second pivotably coupled elongate members. Each of the first and second elongate members has (i) a proximal end portion, and (ii) a distal end portion for engaging a lead. The lead has a proximal end portion having a shoulder. The first and second elongate members are pivotably coupled such that the distal end portions of the first and second elongate members are moveable to allow insertion of the lead proximally past the distal end portions of the elongate members and to allow the distal end portions to engage the lead distal the shoulder. The distal end portions of the first and second members preferably include catches configured to engage the shoulder of the lead to inhibit distal movement of the lead. The connector may include a fulcrum about which the first and second elongate members are pivotable.

Figure 1:
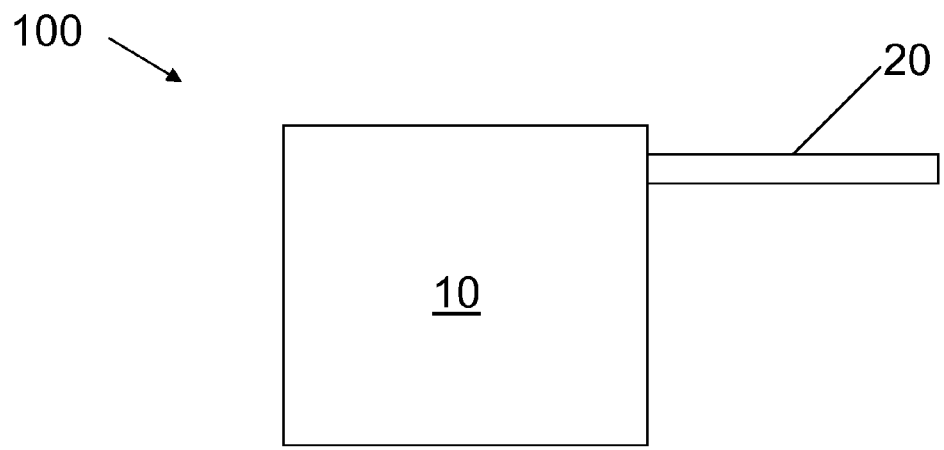
FIG. 1 is a schematic side view of a lead operably coupled to an active implantable medical device.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope of spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "exemplary" or "representative" is used in the sense of "for example" or "for the purposes of illustration", and not in a limiting sense.

Among other things, screw-less connectors for securing a lead relative to an implantable medical device are described herein. Such connectors, in various embodiments, can be easier to implement than a set screw and torque wrench and may result in improved reliability. A connector, as described in various embodiments herein, includes first and second pivotably coupled elongate members. Each of the first and second elongate members has (i) a proximal end portion, and (ii) a distal end portion for engaging a lead. The lead has a proximal end portion having a shoulder. The first and second elongate members are pivotably coupled such that the distal end portions of the first and second elongate members are moveable to allow insertion of the lead proximally past the distal end portions of the elongate members and to allow the distal end portions to engage the lead distal the shoulder. The distal end portions of the first and second members preferably include catches configured to engage the shoulder of the lead to inhibit distal movement of the lead. The connector may include a fulcrum about which the first and second elongate members are pivotable. Nearly any implantable medical device to which a lead connects may be modified to include such connectors. For example, an active implantable medical device or a lead extension may include a connector as described below with reference to FIGS. 5-9 in more detail.

Referring now to FIGS. 1-4, schematic representations of representative implantable medical systems 100 that may employ a connector as described herein are shown. The depicted systems 100 include a lead 20 and an active implantable medical device 10, and may include a lead extension 30. Any suitable active implantable medical device, such as an electrical signal generator for delivering therapy to a patient, an electrical signal receiver for patient monitoring or diagnostics, or the like, may be employed in accordance with the teaching presented herein. Examples of suitable active implantable medical devices include hearing implants; cochlear implants; sensing or monitoring devices; signal generators such as cardiac pacemakers or defibrillators, neurostimulators (such as spinal cord stimulators, brain or deep brain stimulators, peripheral nerve stimulators, vagal nerve stimulators, occipital nerve stimulators, subcutaneous stimulators, etc.), gastric stimulators; or the like.

Figure 2:
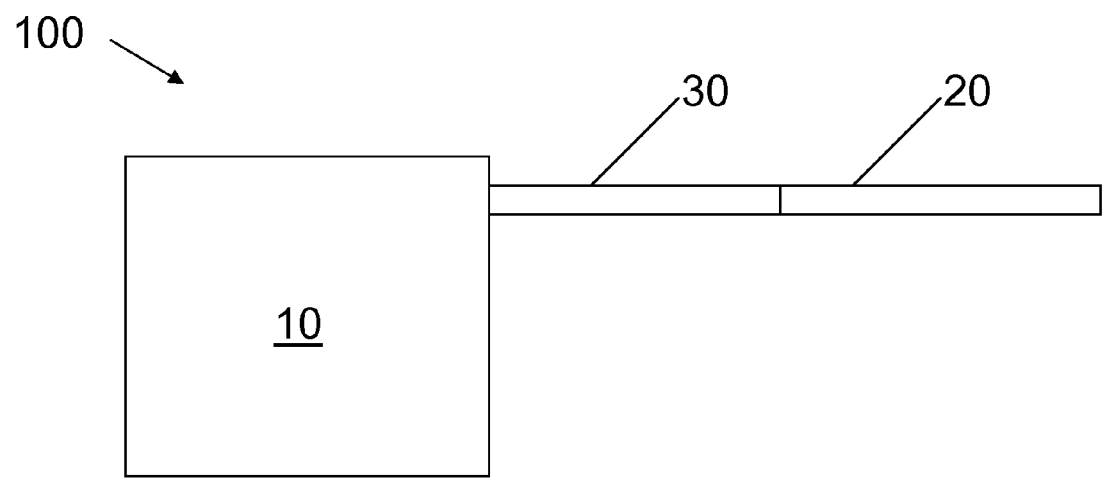
FIG. 2 is a schematic side view of a lead operably coupled to an active implantable medical device via a lead extension.
Figure 3:
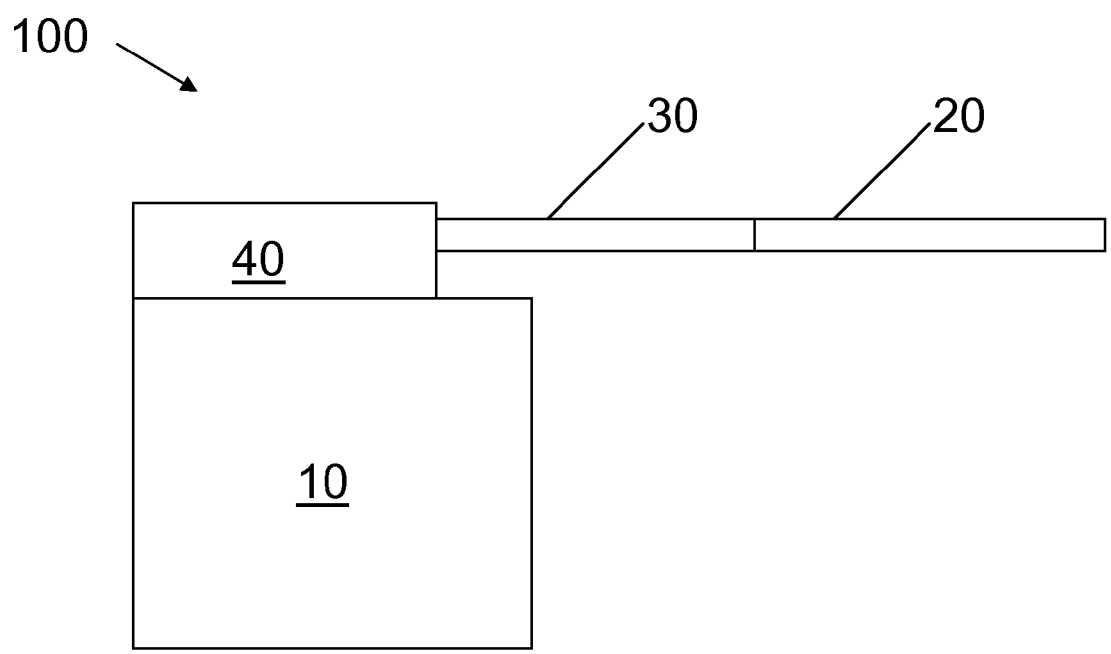
FIG. 3 is a schematic side view of a lead operably coupled to an active implantable medical device via a lead extension, where the implantable medical device includes a connection header.
Figure 4:
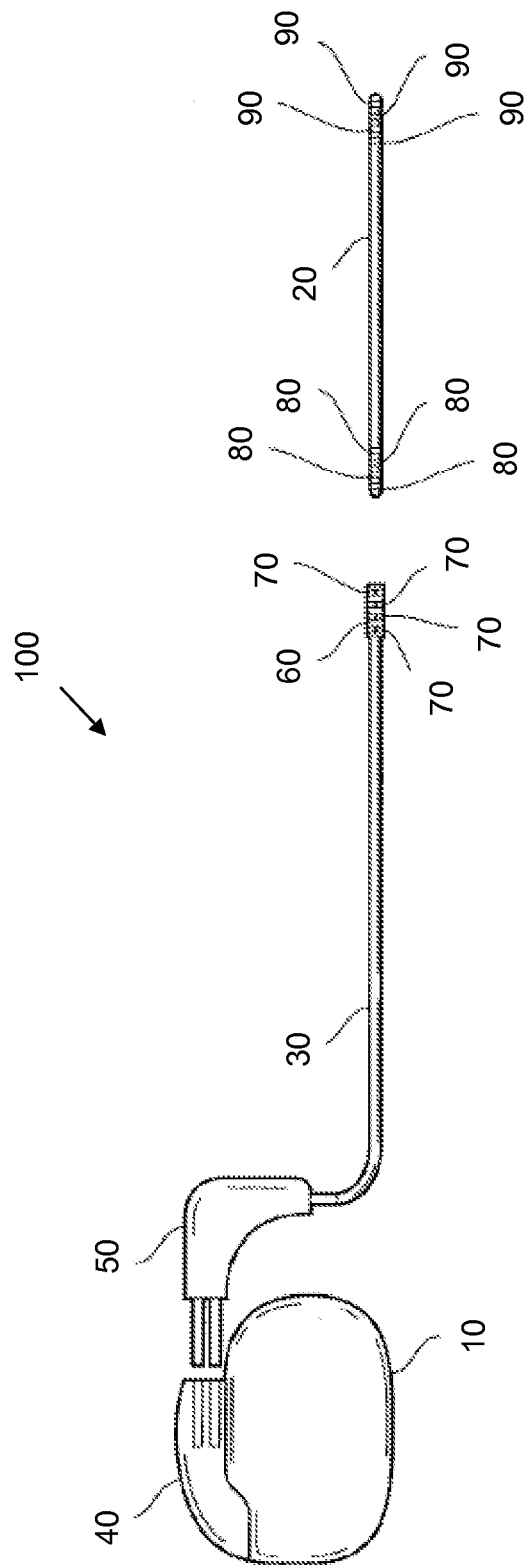
FIG. 4 is a schematic side view of an exemplary lead operably couplable to an active implantable medical device via a lead extension.

As shown in FIG. 1, a lead 20 may be directly coupled to the active medical device 10. Alternatively, a lead 20 may be coupled to the active medical device 10 via a lead extension 30 or suitable adaptor, as shown in FIGS. 2-4. While not shown, it will be understood that more than one lead 20 may be operably coupled to one active electrical device 10 or one extension 30 or adaptor. It will also be understood that more than one extension 30 or adaptor may be operably coupled to one active electrical device 10.

Referring to FIG. 3, active electrical device 10 may include a connector portion 40 for connecting to lead 20 or extension 30 or adaptor to couple lead 20 to active electrical device 10. Of course, the lead 20 may, in various embodiments, be coupled to active electrical device 10 without extension 30 or adaptor.

Referring to FIG. 4, a schematic view of a representative implantable active electrical system 100 is shown. In the system shown in FIG. 4, implantable active electrical device 10 comprises a connector portion 40 configured to receive plug portion 50 at proximal end of extension 30. The distal end of extension 30 comprises a connector portion 60 configured to receive proximal end of lead 20. Connector 60 comprises internal electrical contacts 70 configured to electrically couple extension 30 to lead 20 via electrical contacts 80 disposed on the proximal end portion of lead 20. Electrodes 90 are disposed on distal end portion of lead 20 and are electrically coupled to electrical contacts 80, typically through conductors (not shown). Lead 20 may include any number of electrodes 90, e.g. one, two, three, four, five, six, seven, eight, sixteen, thirty-two, or sixty-four. Typically, each electrode 90 is electrically coupled to a discrete electrical contact 80.

Figure 5A:
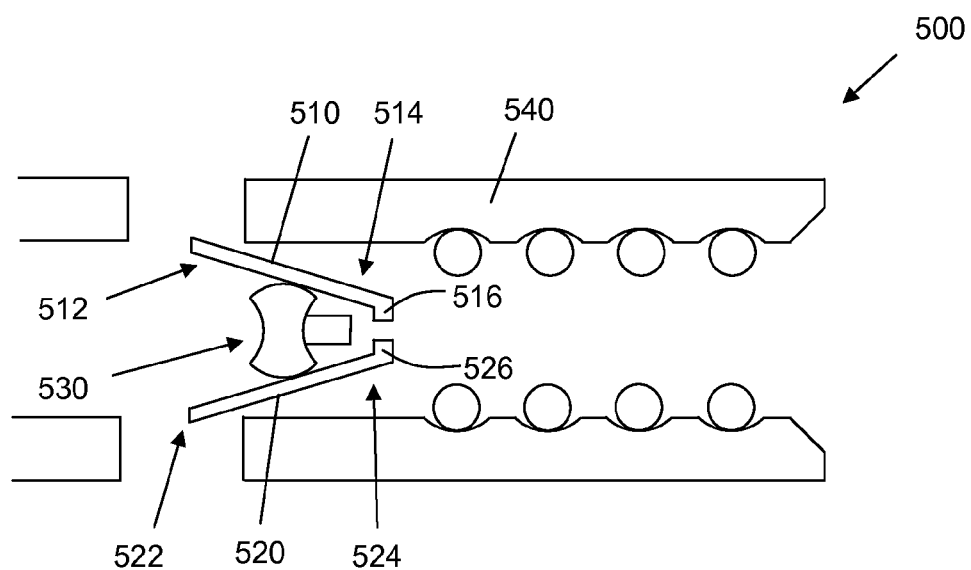
FIG. 5A is a schematic cross-sectional view of some components of a connector.
Figure 5B:
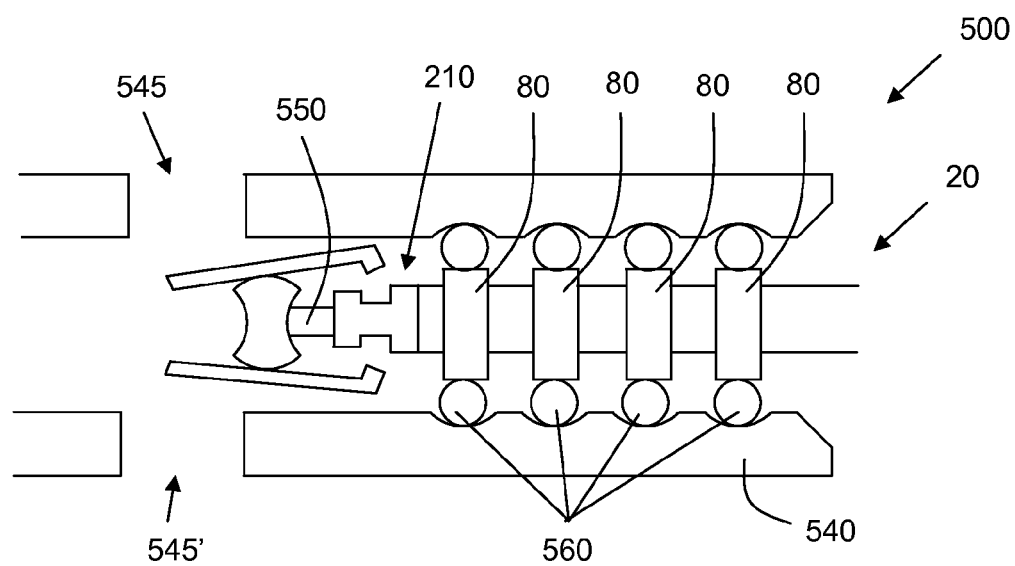
FIGS. 5B-C are schematic cross-sectional views of an exemplary lead and the connector components depicted in FIG. 5A.
Figure 5C:
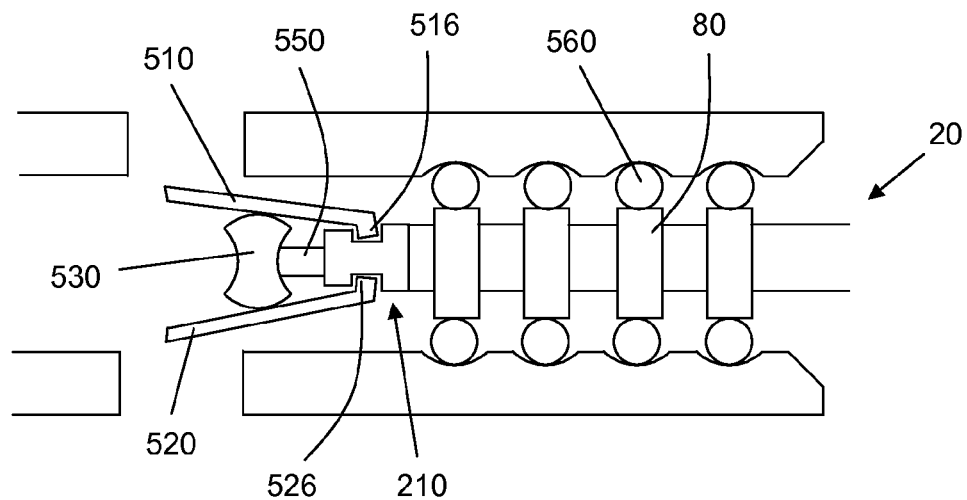

Referring now to FIGS. 5A-C, an embodiment of a connector 500 and lead 20 are shown. As discussed above, the connector 500 may be a part of an active implantable medical device (e.g. a connection header block), a connector portion of a lead extension, or the like. The connector 500 includes first 510 and second 520 elongate members, each having a proximal end portion 512, 522 and a distal end portion 514, 524. The connector also includes a fulcrum 530 positioned between the proximal 512, 522 and distal 514, 524 end portions of the first 510 and second 520 elongate members. The distal end portions 514, 524 may include catches 516, 526, protrusions, or other features configured to engage the lead 20. The elongate members 510, 520 are pivotable about the fulcrum 530 such that the distal end portions 514, 524 are moveable from (i) an engaged position (see, e.g., FIG. 5C) in which the distal end portions 514, 524 engage the lead 20 to inhibit distal movement of the lead 20 relative to the connector 500 to (ii) an open position (see, e.g. FIG. 5B) in which the lead is distally moveable relative to the connector 500. Of course, the elongate members 510, 520 may be pivotably coupled in any suitable manner, regardless of whether the connector 500 includes a fulcrum 530.

In the embodiment depicted in FIG. 5B, a lead 20 is shown disposed in the connector 500. The connector 500 includes a housing 540 having a bore configured to slidably receive the lead 20. The lead 20 may be slid proximally in the connector 500 until the proximal end of the lead 20 engages a stop 550, which prevents or inhibits further proximal movement of the lead 20. The stop 550 may be the fulcrum 530, may be coupled or attached to the fulcrum 530, may be attached to the housing of the connector 500, or the like. The stop 550 is positioned in the housing 540 such that when the lead 20 engages the stop 550, contact rings 80 of the lead 20 engage electrical contacts 560 of the connector 500. In some embodiments, the connector 500 is a component of an active medical device, and the contacts 560 are electrically coupled to electronics of the device. In various embodiments, the connector 500 is a component of a lead extension, and the contacts 560 are electrically coupled to proximal contacts for interfacing with an active medical device.

As shown in FIG. 5C, the elongate members 510, 520 are pivotable about the fulcrum 530 such that catches 516, 526 engage the proximal end portion 210 of the lead 20 at a position distal a shoulder in the proximal end portion 210. When engaged in the manner depicted, distal movement of the lead 20 is prevented or inhibited. The stop 550 and the catches 516, 526 are configured to secure the lead 20 such that the lead contacts 80 are aligned with the contacts 560 of the connector. The proximal end portion 210 of the lead 20 is configured to cooperate with the connector 500 to ensure proper alignment. Additional details regarding features of the proximal end 210 of the lead 20, according to some embodiments, are discussed below with regard to FIGS. 6A-D.

Still referring to FIGS. 5A-C, the connector housing 540 may include openings 545, 545' to allow access to the proximal end portions 512, 522 of proximal end portions 512, 522 so that a relative inward force may be applied to the proximal end portions 512, 522 of the elongate members 510, 520. The proximal end portions 512, 522 may be squeezed manually or through the use of a tool (not shown) configured to fit through the openings 545, 545' to apply the relative inward force (i.e., a force that brings the proximal end portions 512, 522 closer together). A flexible or resilient material (not shown), such as silicone, may sealingly engage the opening to permit the force to be applied to the proximal end portions 512, 522 of the elongate members 510, 520, while preventing body fluids from entering the interior of the housing 540 when the connector 500 is implanted in the patient.

With reference to FIG. 5A, the distal end portions 514, 524 of the elongate members 510, 520 may be biased towards a closed position in which the closest distance between the distal end portion 514 of the first elongate member 510 and the distal end portion 524 of the second elongate member 520 is less than the outer diametric dimension of the region of the lead that the distal end portions 514, 524 are configured to engage. Any suitable spring or resilient force mechanism, including the outer elastomeric wall of the connector, may be employed to cause the distal end portions 514, 524 to be biased towards the closed position. By being biased to the closed position, the distal end portions 514, 524 can engage an inserted lead (see, e.g. FIG. 5C) distal a shoulder on the lead to prevent or inhibit distal movement of the engaged lead.

Referring now to FIGS. 6A-D, schematic cross-sections of an embodiment of a proximal portion 210 of a lead and components of a connector are shown. The proximal end portion 210 of the lead includes a shoulder 220 distal the proximal end. In the depicted embodiment, an indent region 230 or groove forms the shoulder 220. The lead's proximal end portion 210 may also include a ramped portion 240 to facilitate insertion into the engagement portion of the connector. The ramped portion 240 may be tapered, rounded or otherwise configured to facilitate insertion; e.g., as described below.

The components of the connector depicted in FIGS. 6A-D include the elongate members 510, 520, which have proximal end portions 512, 522 and distal end portions 514, 524, a fulcrum 530 and a stop 550, which may be a portion of the fulcrum 530 or may be a separate component. The distal end portions 514, 524 include catches 516, 526 configured to engage the shoulder 220 of the lead. The distal end portions 514, 524 of the elongate members 510, 520 also include ramped portions 518, 528 configured to facilitate insertion of the distal end portion 210 of the lead into the engagement portion of the connector.

Figure 6A:
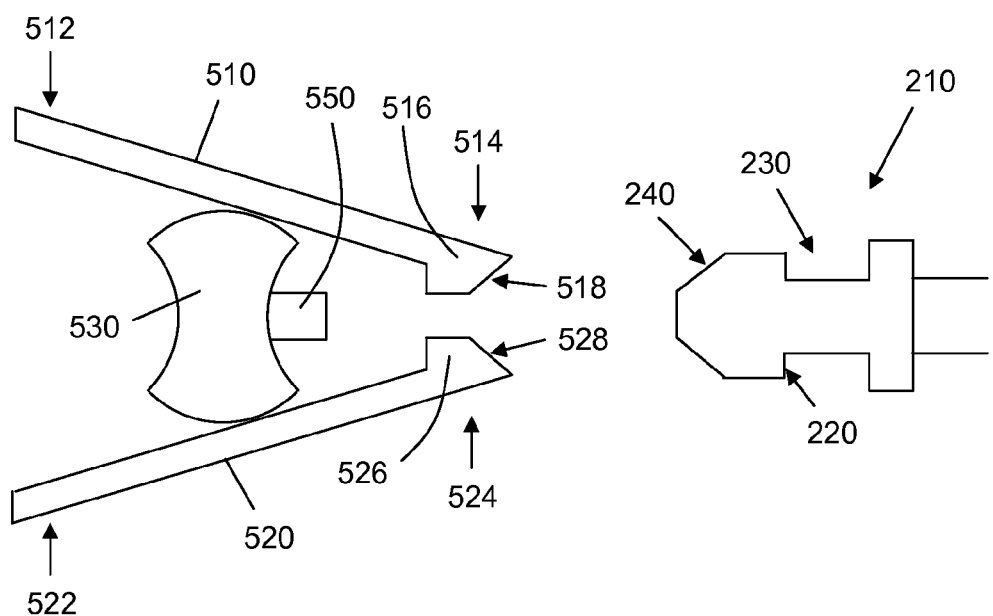
FIGS. 6A-D are schematic cross-sectional views of an exemplary lead and some components of an exemplary connector.
Figure 6B:
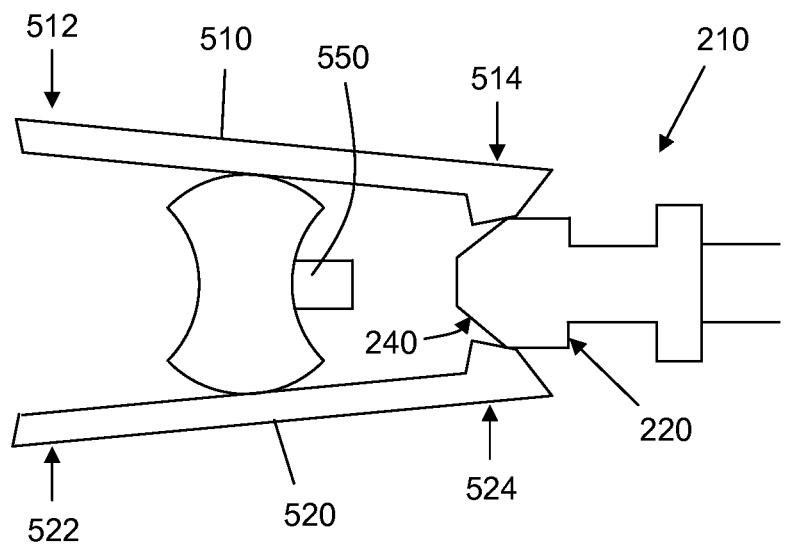
Figure 6C:
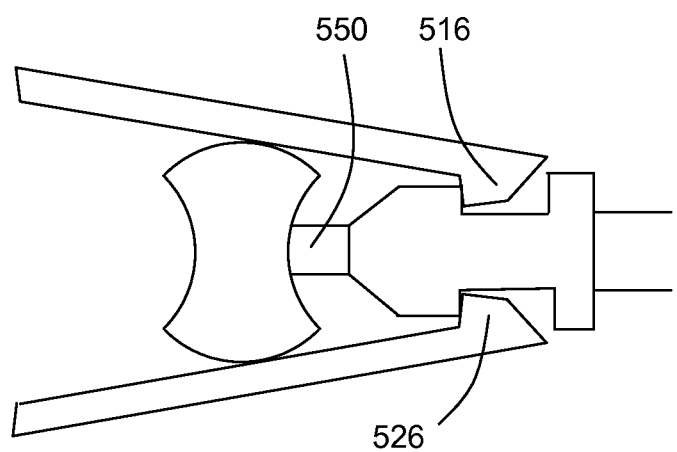
Figure 6D:
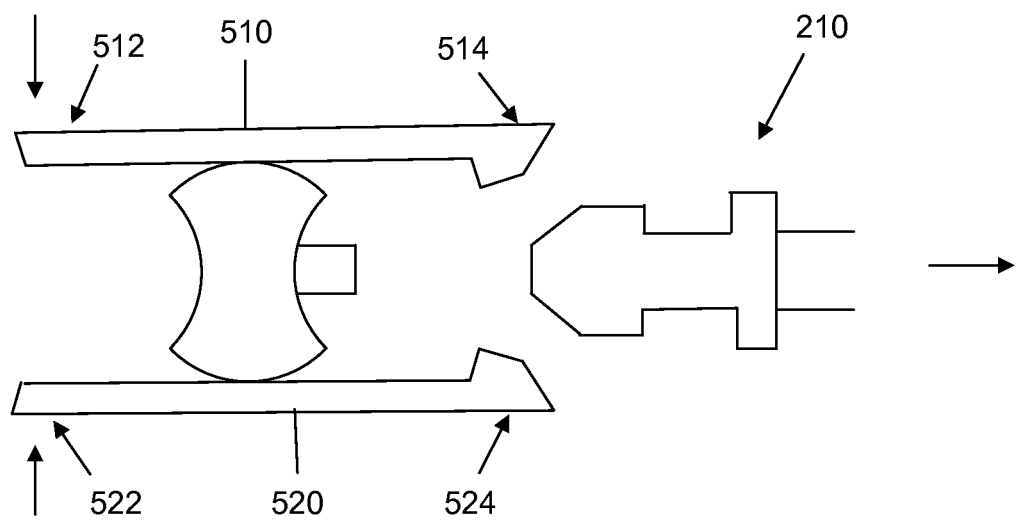

The distal end portions 514, 524 of the elongate elements 510, 520 depicted in FIGS. 6A-D are preferably biased towards a closed position (see, e.g., FIG. 6A) in which the closest distance between the distal end portion 514 of the first elongate member 510 and the distal end portion 524 of the second elongate member 520 is less than the outer diametric dimension of the region of the lead that the distal end portions 514, 524 are configured to engage. As shown in FIG. 6B, as the lead is moved proximally along the ramped portions 518, 528 of the elongate members 510, 520, the distal end portions 514, 524 of the elongate members 510, 520 move apart to allow further proximal insertion of the lead. As indicated, the proximal end portion 210 of the lead may also include a ramped portion 240 to facilitate the insertion process. The lead may be inserted until the proximal end of the lead engages the stop 550 (see, e.g., FIG. 6C). As the proximal end portion 210 of the lead is moved proximally towards the stop 550, the catches 516, 526 engage the shoulder 220 of the lead, preventing or inhibiting distal movement of the lead relative to the connector. The biasing force of the distal end portions 514, 524 of the elongate members 510, 520 towards the closed position facilitate the engagement of the shoulder 220 of the lead by the catches 516, 526. As shown in FIG. 6D, application of relative inward force (e.g. squeezing in the direction of the depicted arrows) of the proximal end portions 512, 522 of the elongate members 510, 520 causes the distal end portions 514, 524 to move apart, allowing the lead to be moved distally relative to the connector.

The connector embodiment depicted in FIGS. 6A-D allows for tool-less insertion of a lead. The ability to insert the lead without concomitant squeezing of the proximal end portions 512, 522 of the elongate members 510, 520 of the connector may be desirable to reduce implant time and potential procedural error. To remove the lead, the proximal end portions 512, 522 of the elongate members 510, 520 may be squeezed with a person's fingers or through use of a tool. In many situations, once a lead is inserted, there is no need or desire to remove the lead unless a lead malfunction occurs or other issue arises.

Figure 7A:
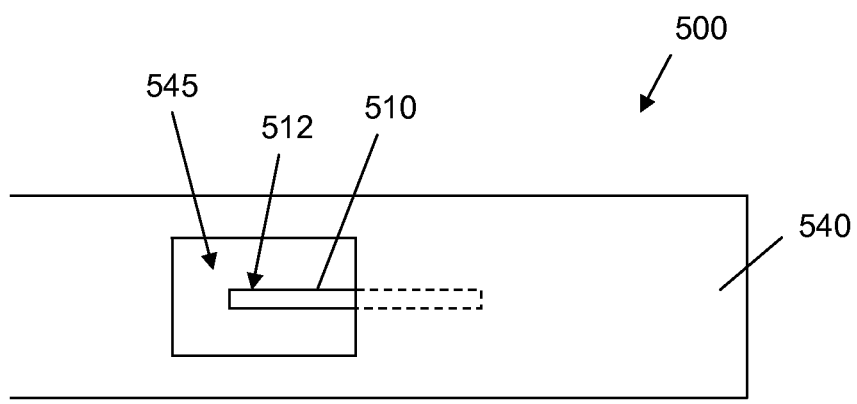
FIGS. 7A-B are schematic side views of an exemplary connector having a housing with an opening.
Figure 7B:
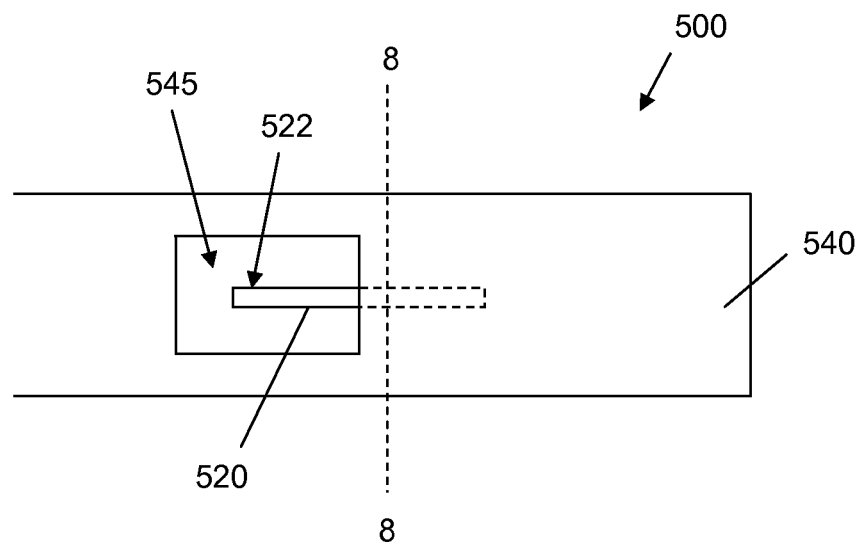

Referring now to FIGS. 7A and 7B, opposing schematic side views (or opposing top-down and bottom-up views, or the like) of a representative connector 500 are shown. In the depicted embodiment, an opening 545 in the housing 540 of the connector 500 provides access to the proximal end portions 512, 522 of the elongate members 510, 520 such that relative inward force may be applied to the proximal ends 512, 522 of the pivotably coupled elongate members 510, 520. The dashed lines indicate the elongate members 510, 520 extending distally within the housing 540. A cover (not shown) may sealingly engage the opening to prevent or inhibit body fluids from entering the interior of the housing 540 through the opening 545 when implanted. The cover may be made of material that is sufficiently resilient or flexible to allow maintenance of a seal while allowing access to the proximal end portions 512, 522 of the elongate members 510, 520.

Figure 8:
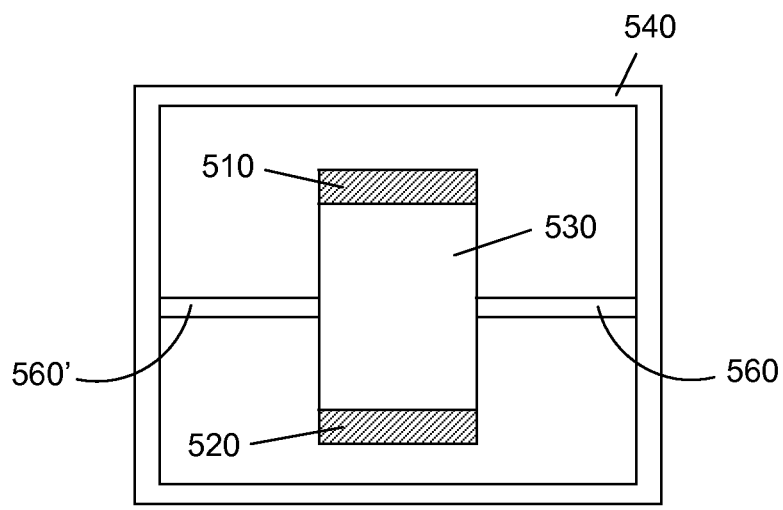
FIG. 8 is a schematic cross-sectional view of an embodiment of a connector depicted in FIGS. 7A-B taken along line 8-8 as shown in FIG. 7B.
Figure 9:
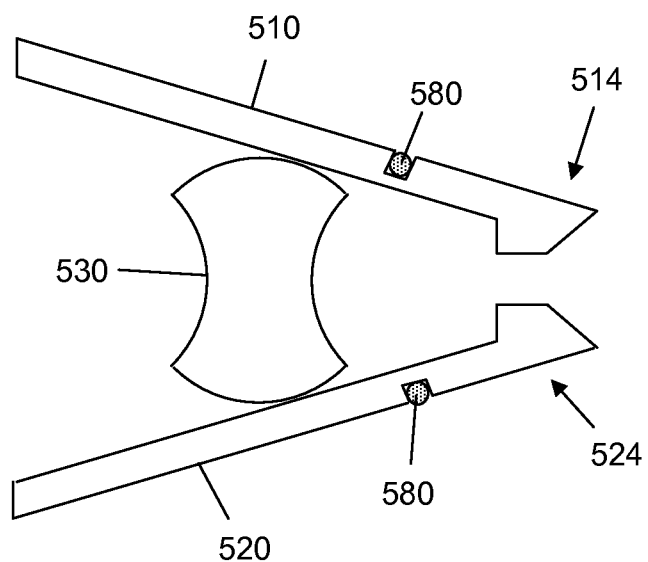
FIG. 9 is a schematic cross-sectional view of some components of an exemplary connector.

FIG. 8 is a schematic cross-sectional view taken along line 8-8 of FIG. 7B at a location where the elongate members 510, 520 are in contact with fulcrum 530. The fulcrum 530 in the depicted embodiment is anchored to the housing 540 of the connector via arms 560, 560'. Of course, the fulcrum may be coupled to the housing through any other suitable mechanism. In some embodiments, two or more of the fulcrum 530, arms 560, 560' and housing 540 are a single unit. The single unit may be molded or otherwise formed. When made of separate units, the fulcrum 530, arms 560, 560' and housing 540 may be attached or coupled via welding, adhesive, fastener, or any other suitable mechanism.

In some embodiments, the fulcrum and the elongate members of a connector are a single unit. The single unit is made of material that allows the elongate members to pivot about the fulcrum. For example, a single unit may be made of any suitable polymeric material or metallic material. Preferably, the material is sufficiently resilient to allow the distal end portions of the elongate members to be biased towards a closed position and moved to an open position (e.g., as described above). In some embodiments, such a single unit is formed from temperature affected material or shape memory material, such as nitinol.

In some embodiments, the fulcrum and the elongate members are separate units that are operably coupled such that the elongate members are pivotable about the fulcrum (e.g., as described above). In some embodiments, a spring or other suitable resilient force mechanism may be employed to cause the distal end portions of the elongate members to be biased towards a closed position. For example, and with reference to FIG. 9, a schematic cross sectional view of representative components of a connector are shown, in which elongate members 510, 520 are pivotable about a fulcrum 530. The distal end portions 514, 524 are biased in a closed position by a spring or elastic band 580 wrapped about the elongate members 510, 520 distal the fulcrum 530. In the depicted embodiment, the spring 580 or band is positioned in a groove in the first elongate member 510 and a groove in the second elongate member 520. Of course, any other mechanism for retaining the spring or band may be employed.

Any suitable material may be used to form a fulcrum or elongate members as described herein. In various embodiments, a fulcrum or elongate member, or portions thereof, are formed from a metallic material or rigid plastic material.

Connectors, as described herein, may form a part of an implantable active medical device (e.g., a connector header), a distal end portion of a lead extension or adaptor, or the like. It will be understood that a "lead" that may be coupled with a connector may be a lead extension; e.g., if the connector is part of an active implantable medical device.

Thus, embodiments of the CONNECTOR FOR IMPLANTABLE MEDICAL LEAD are disclosed. One skilled in the art will appreciate that the connectors, leads, systems, and methods described herein can be practiced with embodiments other than those disclosed. The disclosed embodiments are presented for purposes of illustration and not limitation.

What is claimed is:

1. An implantable medical connector for electrically coupling a medical lead to an implantable medical device, wherein the lead comprises a proximal end portion having a shoulder, the connector comprising:
   a first elongate member having (i) a proximal end portion, and (ii) a distal end portion configured to engage the lead; and
   a second elongate member having (i) a proximal end portion, and (ii) a distal end portion configured to engage the lead,
   wherein the first elongate member is pivotably coupled to the second elongate member such that the distal end portions of the first and second elongate members are moveable to allow insertion of the lead past the distal end portions of the elongate members and to allow the distal end portions to engage the lead shoulder;
   a fulcrum positioned between proximal and distal end portions of the first and second elongate members, wherein the first and second elongate members are pivotable about the fulcrum;
   wherein the first and second elongate members are pivotable such that the distal end portions of the first and second elongate members are moveable from (i) an engaged position in which the distal end portions are configured to engage the lead to inhibit movement of the lead distally relative to the elongate members to (ii) an open position in which the closest distance between the distal end portions of the first and second elongate members is greater than the outer diametric dimension of the proximal end portion of the lead, at or proximal the shoulder, to permit the lead to be distally moved relative to the elongate members; and
   wherein the distal end portions of the first and second elongate members are moveable from the engaged position to the open position by application of relative inward force on the proximal end portions of the first and second elongate members.

2. An implantable medical connector according to claim 1, wherein the distal end portion of the first members comprises a catch configured to engage the shoulder of the lead, and wherein the distal end portion of the second elongate member comprises a catch configured to engage the shoulder of the lead.

3. A system comprising:
   an implantable medical lead having a proximal end portion comprising a shoulder; and
   an implantable medical connector for electrically coupling the lead to an implantable medical device, the connector comprising:
      a first elongate member having (i) a proximal end portion, and (ii) a distal end portion configured to engage the lead shoulder;
      a second elongate member having (i) a proximal end portion, and (ii) a distal end portion configured to engage the lead shoulder; and
      a fulcrum positioned between proximal and distal end portions of the first and second elongate members,
      wherein the first and second elongate members are pivotable about the fulcrum such that the distal end portions of the first and second elongate members are moveable from (i) an engaged position in which the distal end portions are configured to engage the lead shoulder to inhibit movement of the lead distally relative to the elongate members to (ii) an open position in which the closest distance between the distal end portions of the first and second elongate members is greater than the outer diametric dimension of the lead at, or proximal to, the shoulder to permit the lead be distally moved relative to the elongate members; and
   wherein the distal end portions of the first and second elongate members are moveable from the engaged position to the open position by application of relative inward force on the proximal end portions of the first and second elongate members.

4. An implantable medical connector for electrically coupling a medical lead to an implantable medical device, wherein the lead comprises a proximal end portion having a shoulder, the connector comprising:
   a first elongate member having (i) a proximal end portion, and (ii) a distal end portion configured to engage the lead; and
   a second elongate member having (i) a proximal end portion, and (ii) a distal end portion configured to engage the lead,
   wherein the first elongate member is pivotably coupled to the second elongate member such that the distal end portions of the first and second elongate members are moveable to allow insertion of the lead past the distal end portions of the elongate members and to allow the distal end portions to engage the lead shoulder;
   a fulcrum positioned between proximal and distal end portions of the first and second elongate members, wherein the first and second elongate members are pivotable about the fulcrum;
   wherein the connector further comprises a housing configured to slidably receive the proximal end portion of the lead, wherein the first and second elongate members are disposed in the housing; and
   wherein a first opening is formed in the housing to provide access to the proximal end portion of the first elongate member, and a second opening is formed in the housing to provide access to the proximal end portion of the second elongate member.

5. A system comprising:
   the connector according to claim 4; and
   the lead having the proximal end portion configured to be engaged by the connector.

6. A connector according to claim 1, wherein the connector further comprises a housing configured to slidably receive the proximal end portion of the lead, wherein the first and second elongate members are disposed in the housing.

7. A connector according to claim 6, wherein a first opening is formed in the housing to provide access to the proximal end portion of the first elongate member, and a second opening is formed in the housing to provide access to the proximal end portion of the second elongate member.

8. A connector according to claim 1, wherein the distal end portions of the first and second elongate members comprise ramped portions configured to cause the distal end portions of the elongate members to move apart when the proximal portion of the lead is moved proximally along the ramped portions.

9. A connector according to claim 1, wherein the first and second elongate members are biased towards a closed position in which the closest distance between the distal end portions of the first and second elongate members is less than the outer diametric dimension of the portion of the proximal end portion of the lead that the distal end portions of the elongate members are configured to engage.

10. A connector according to claim 1, further comprising a stop element positioned and configured to engage the proximal end portion of the lead and to prevent further proximal movement of the lead relative to the connector.

11. An active implantable medical device comprising a connector according to claim 1.

12. An active implantable medical device according to claim 11, wherein the device is an implantable electrical signal generator.

13. A lead extension comprising a connector according to claim 1.

14. A system comprising:
the connector according to claim 1; and
the lead having the proximal end portion configured to be engaged by the connector.

15. A system according to claim 14, further comprising the implantable medical device to which the connector is configured to operably couple the lead.

16. A system according to claim 15, wherein the implantable medical device is an active implantable medical device.

17. A system according to claim 16, wherein the active implantable medical device is an implantable electrical signal generator.

18. A system according to claim 15, wherein the implantable medical device is a lead extension.

19. A system according to claim 15, wherein the implantable medical device comprises the connector.

* * * * *